(12) United States Patent
Jippo

(10) Patent No.: US 11,579,102 B2
(45) Date of Patent: Feb. 14, 2023

(54) INFORMATION PROCESSING APPARATUS, INFORMATION PROCESSING METHOD, AND INFORMATION PROCESSING PROGRAM

(71) Applicant: FUJITSU LIMITED, Kawasaki (JP)

(72) Inventor: Hideyuki Jippo, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 607 days.

(21) Appl. No.: 16/778,310

(22) Filed: Jan. 31, 2020

(65) Prior Publication Data

US 2020/0309722 A1 Oct. 1, 2020

(30) Foreign Application Priority Data

Mar. 29, 2019 (JP) .............................. JP2019-066571

(51) Int. Cl.
| | |
|---|---|
| *C09K 21/08* | (2006.01) |
| *G01N 25/22* | (2006.01) |
| *G16C 20/70* | (2019.01) |
| *G16C 20/10* | (2019.01) |

(52) U.S. Cl.
CPC .............. *G01N 25/22* (2013.01); *G16C 20/10* (2019.02); *G16C 20/70* (2019.02)

(58) Field of Classification Search
CPC .... C08K 5/0066; C08L 2201/02; G01N 25/22
See application file for complete search history.

(56) References Cited

U.S. PATENT DOCUMENTS 7,258,823 B2 * 8/2007 Feske ................... C08K 5/0066
560/92
2016/0002517 A1 1/2016 Itakura et al.

FOREIGN PATENT DOCUMENTS

| EP | WO 2106/182030 | * 11/2016 |
|---|---|---|
| JP | 2013-519776 A | 5/2013 |
| JP | 2016-14100 A | 1/2016 |
| WO | 2011/101618 A2 | 8/2011 |

OTHER PUBLICATIONS

ISO copyright office; "Refrigerants—Designation and safety classification", International Standard ISO817, May 15, 2014, Third edition, pp. 1-73 (Total 80 pages), cited in specification.

* cited by examiner

*Primary Examiner* — Lam S Nguyen
(74) *Attorney, Agent, or Firm* — WHDA, LLP

(57) ABSTRACT

An information processing method is performed by a computer for evaluating flammability of a mixed refrigerant material containing a plurality of components. The method includes: calculating, for each of the plurality of components, a second value obtained by multiplying a mixture ratio thereof in the mixed refrigerant material by a first value obtained based on numbers of hydrogen atoms, halogen atoms, and double bonds included in a molecular structure thereof; calculating a total sum of the second value calculated for each of the plurality of components; and classifying the mixed refrigerant material into a predetermined flammability class based on the total sum.

7 Claims, 10 Drawing Sheets

FIG. 9A

| MIXED REFRIGERANT MATERIAL | COMPONENT 1 | COMPONENT 2 | COMPONENT 3 | FLAMMABILITY CLASS OF COMPONENT 1 | FLAMMABILITY CLASS OF COMPONENT 2 | FLAMMABILITY CLASS OF COMPONENT 3 | MIXTURE RATIO OF COMPONENT 1 $y_1$ | MIXTURE RATIO OF COMPONENT 2 $y_2$ | MIXTURE RATIO OF COMPONENT 3 $y_3$ | FLAMMABILITY CLASS OF MIXED REFRIGERANT MATERIAL (CLASSIFIED BY EXPERIMENT) |
|---|---|---|---|---|---|---|---|---|---|---|
| R433B | R1270 | R290 | | 3 | 3 | | 0.05 | 0.95 | | 3 |
| R433C | R1270 | R290 | | 3 | 3 | | 0.25 | 0.75 | | 3 |
| R436A | R290 | R600a | | 3 | 3 | | 0.56 | 0.44 | | 3 |
| R436B | R290 | R600a | | 3 | 3 | | 0.52 | 0.48 | | 3 |
| R433A | R1270 | R290 | | 3 | 3 | | 0.3 | 0.7 | | 3 |
| R511A | R290 | R152a | | 3 | 2 | | 0.95 | 0.05 | | 3 |
| R432A | R1270 | E170 | | 3 | 3 | | 0.8 | 0.2 | | 3 |
| R431A | R290 | R152a | | 3 | 2 | | 0.71 | 0.29 | | 3 |
| R429A | R170 | R152a | R600a | 3 | 2 | 3 | 0.6 | 0.1 | 0.3 | 3 |
| R510A | RE170 | R600a | | 3 | 3 | | 0.88 | 0.12 | | 3 |
| R435A | R170 | R152a | | 3 | 2 | | 0.8 | 0.2 | | 3 |
| R430A | R152a | R600a | | 2 | 3 | | 0.76 | 0.24 | | 3 |
| R440A | R290 | R134a | R152a | 3 | 1 | 2 | 0.06 | 0.02 | 0.98 | 2 |
| R512A | R134a | R152 | | 1 | 2 | | 0.05 | 0.95 | | 2 |
| R415B | R22 | R152a | | 1 | 2 | | 0.25 | 0.75 | | 2 |
| R411A | R1270 | R22 | R152a | 3 | 1 | 2 | 0.02 | 0.88 | 0.11 | 2 |
| R415A | R22 | R152a | | 1 | 2 | | 0.82 | 0.18 | | 2 |
| R411B | R1270 | R22 | E170 | 3 | 1 | 3 | 0.03 | 0.94 | 0.03 | 2 |
| R419A | R125 | R134a | R142b | 1 | 1 | 2 | 0.77 | 0.19 | 0.04 | 2 |
| R406A | R22 | R600a | R600 | 1 | 3 | 3 | 0.55 | 0.04 | 0.41 | 2 |
| R439A | R32 | R125 | R152a | 2 | 1 | 2 | 0.5 | 0.47 | 0.03 | 2 |
| R418A | R290 | R22 | R152a | 3 | 1 | 2 | 0.02 | 0.96 | 0.03 | 2 |
| R412A | R22 | R218 | R142b | 1 | 1 | 2 | 0.7 | 0.05 | 0.25 | 2 |
| R413A | R218 | R134a | R600a | 1 | 1 | 3 | 0.09 | 0.88 | 0.03 | 2 |

FROM FIG. 9A

| | | | | | | | | | | | |
|---|---|---|---|---|---|---|---|---|---|---|---|
| R403A | R290 | R22 | R218 | | 3 | 1 | 1 | 0.05 | 0.75 | 0.2 | 2 |
| R419B | R125 | R134a | E170 | | 1 | 1 | 3 | 0.49 | 0.48 | 0.04 | 2 |
| R446A | R32 | R1234ze | R600a | | 2 | 2 | 3 | 0.68 | 0.29 | 0.03 | 2 |
| R447A | R32 | R125 | R1234ze | | 2 | 1 | 2 | 0.68 | 0.04 | 0.29 | 2 |
| R451A | R1234yf | R134a | | | 2 | 1 | 0 | 0.9 | 0.1 | | 2 |
| R451B | R1234yf | R134a | | | 2 | 1 | 0 | 0.89 | 0.11 | | 2 |
| R452B | R32 | R125 | R1234yf | | 2 | 1 | 2 | 0.67 | 0.07 | 0.26 | 2 |
| R454A | R32 | R1234yf | | | 2 | 2 | | 0.35 | 0.65 | | 2 |
| R454B | R32 | R1234yf | | | 2 | 2 | | 0.69 | 0.31 | | 2 |
| R454C | R32 | R1234yf | | | 2 | 2 | | 0.22 | 0.79 | | 2 |
| R443A | R1270 | R290 | R600a | | 2 | 2 | 2 | 0.55 | 0.4 | 0.05 | 3 |
| R404A | R143a | R125 | R134a | | 2 | 1 | 1 | 0.52 | 0.44 | 0.04 | 1 |
| R407A | R32 | R125 | R134a | | 2 | 1 | 1 | 0.2 | 0.4 | 0.2 | 1 |
| R407C | R32 | R125 | R134a | | 2 | 1 | 1 | 0.23 | 0.25 | 0.52 | 1 |
| R407F | R32 | R125 | R134a | | 2 | 1 | 1 | 0.3 | 0.3 | 0.4 | 1 |
| R410A | R32 | R125 | | | 2 | 1 | | 0.5 | 0.5 | | 1 |
| R450A | R1234ze | R134a | | | 1 | 1 | | 0.58 | 0.42 | | 1 |
| R452A | R1234yf | R32 | R125 | | 1 | 2 | 2 | 0.3 | 0.11 | 0.59 | 1 |
| R500 | R12 | R152a | | | 1 | 2 | | 0.74 | 0.26 | | 1 |
| R501 | R22 | R12 | | | 1 | 1 | 0 | 0.75 | 0.25 | | 1 |
| R502 | R22 | R115 | | | 1 | 1 | 0 | 0.49 | 0.51 | | 1 |
| R503 | R23 | R13 | | | 1 | 1 | | 0.4 | 0.6 | | 1 |
| R504 | R32 | R115 | | | 2 | 1 | 0 | 0.48 | 0.52 | | 1 |
| R507A | R143a | R125 | | | 2 | 1 | | 0.5 | 0.5 | | 1 |
| R513A | R1234yf | R134a | | | 2 | 1 | 0 | 0.56 | 0.44 | | 1 |

INFORMATION PROCESSING APPARATUS, INFORMATION PROCESSING METHOD, AND INFORMATION PROCESSING PROGRAM

CROSS-REFERENCE TO RELATED APPLICATION

This application is based upon and claims the benefit of priority of the prior Japanese Patent Application No. 2019-66571, filed on Mar. 29, 2019, the entire contents of which are incorporated herein by reference.

FIELD

The embodiments described herein are related to an information processing apparatus, an information processing method, and an information processing program.

BACKGROUND

In recent years, a mixed refrigerant material obtained by mixing pure refrigerant materials has been developed as a refrigerant used in an air conditioner or a refrigerator. For a pure refrigerant material, it is difficult to simultaneously achieve both a cooling function derived from physical properties such as boiling point and thermal conductivity and environmental performance such as lowering global warming potential, but both of these may be simultaneously achieved with a mixed refrigerant material. Therefore, by using the mixed refrigerant material, energy efficiency of an air conditioner, a refrigerator, or the like may be improved while suppressing an environmental load.

Improvement in performance and high flame retardancy are required for a refrigerant material for safety of the product. The physical properties of a mixed refrigerant material having flame retardancy are varied depending on mixture components and mixture ratio of the mixed refrigerant material. There are 60 or more kinds of existing pure refrigerant materials, and the number of combinations of mixture components and mixture ratio of mixed refrigerant materials is enormous. Therefore, due to time limitation, it is not practical to obtain information on physical properties and flame retardancy by experimenting all the combinations of mixture components and mixture ratio.

Therefore, a method of predicting flammability of a mixed refrigerant material whose physical properties are unknown, from a combination of mixture components and mixture ratio thereof, and also investigating other physical properties of a mixed refrigerant material expected to be flame retardant is considered to be a method for shortening the time for development of the refrigerant material.

As the method of predicting the flammability of the mixed refrigerant material, a method of quantifying the tendency of flammability from a combination of mixture components and mixture ratio of a mixed refrigerant material whose flammability is already known and predicting the flammability based on a combination of mixture components and mixture ratio of a mixed refrigerant material whose flammability is unknown and the tendency of flammability may be considered.

The international standard ISO817 of refrigerant is known as an indicator of the tendency of flammability, and the flammability class of pure refrigerant material obtained in combustion experiment is roughly divided into the following three.

Class 1: inflammable (flame propagation does not occur)

Class 2: flame retardant (combustion limit ≥3.5 vol % & combustion heat <19 MJ/kg)

Class 3: highly flammable (combustion limit <3.5 vol % or combustion heat ≥19 MJ/kg)

For a mixed refrigerant material containing a pure refrigerant material classified into a flammability class described above as a component, a method of using a value obtained by multiplying the flammability class of each component by a mixture ratio as an evaluation index is considered. Vol % means the volume ratio with respect to air, and MJ/kg means mega-joule/kilo-gram.

It is known that the flammability of a mixture is related to the ratio of carbon-fluorine bonds to carbon-hydrogen bonds (see, for example, Japanese National Publication of International Patent Application No. 2013-519776).

When a flammability evaluation index is obtained by multiplying the flammability class of a pure refrigerant material by a mixture ratio and or the flammability evaluation index is obtained in consideration of one parameter related to the molecular structure of the pure refrigerant material, the value of the flammability evaluation index becomes non-linear, and thus it is impossible to distinguish the flammability. This is because the flammability evaluation index as described above does not reflect exceptional change in the physical properties caused by mixing of pure refrigerant materials.

When the value of the flammability evaluation index is non-linear, for example, the flammability class 1 and the flammability class 2 are not distinguished from each other. The flammability is not predicted from the combination of mixture components and mixture ratio of the mixed refrigerant material, and an additional experiment for verifying flammability is required.

Accordingly, it is an object of a first aspect of the embodiments to provide an information processing apparatus capable of improving the prediction accuracy of flammability.

SUMMARY

According to an aspect of the embodiments, an information processing method is performed by a computer for evaluating flammability of a mixed refrigerant material containing a plurality of components. The method includes: calculating, for each of the plurality of components, a second value obtained by multiplying a mixture ratio thereof in the mixed refrigerant material by a first value obtained based on numbers of hydrogen atoms, halogen atoms, and double bonds included in a molecular structure thereof; calculating a total sum of the second value calculated for each of the plurality of components; and classifying the mixed refrigerant material into a predetermined flammability class based on the total sum.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 9A and 9B are tables illustrating the flammability of existing mixed refrigerant materials.

DESCRIPTION OF EMBODIMENTS

An information processing apparatus according to a first embodiment will be described. The information processing apparatus according to the first embodiment is an apparatus for evaluating the flammability of a mixed refrigerant material.

Figure 1:
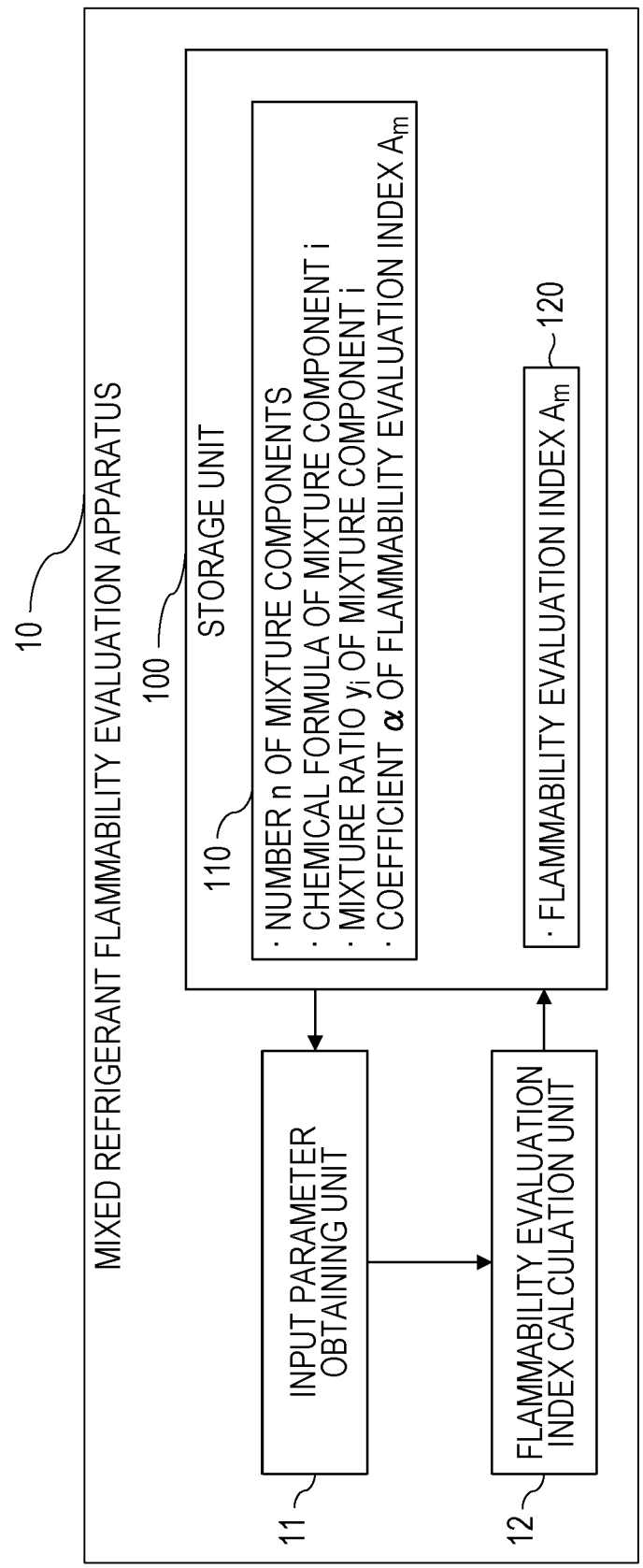
FIG. 1 is a diagram illustrating an information processing apparatus according to a first embodiment.

FIG. 1 is a diagram illustrating the information processing apparatus according to the first embodiment. As illustrated in FIG. 1, a mixed refrigerant flammability evaluation apparatus 10 includes an input parameter obtaining unit 11, a flammability evaluation index calculation unit 12, and a storage unit 100. The input parameter obtaining unit 11 is coupled to the storage unit 100, the flammability evaluation index calculation unit 12 is coupled to the input parameter obtaining unit 11, and the storage unit 100 is coupled to the flammability evaluation index calculation unit 12.

The input parameter obtaining unit 11 reads input parameters 110 stored in the storage unit 100. The input parameters 110 read by the input parameter obtaining unit 11 are sent to the flammability evaluation index calculation unit 12 as variables of a flammability evaluation index $A_m$ that will be described later. The flammability evaluation index calculation unit 12 calculates the flammability evaluation index $A_m$ based on the input parameters 110 that have been sent thereto. The storage unit 100 stores the flammability evaluation index $A_m$ calculated by the flammability evaluation index calculation unit 12 as an output parameter 120.

The storage unit 100 stores, as the input parameters 110, the number n of mixture components, a chemical formula of a mixture component i, a mixture ratio $y_i$ of the mixture component i, and a coefficient α of the flammability evaluation index $A_m$, which are information related to components of a mixed refrigerant material whose flammability is to be evaluated.

The input parameter obtaining unit 11 and the flammability evaluation index calculation unit 12 are, for example, a central processing unit (CPU). The storage unit 100 is, for example, a random-access memory (RAM) or a hard disk.

A flammability evaluation method according to a comparative example of an information processing apparatus will be described. In the flammability evaluation method according to the comparative example, the total sum of values of respective components of the mixed refrigerant material each of which is obtained by multiplying the flammability class of the mixture component i determined by the combustion test by the mixture ratio $y_i$ of the mixture component i is calculated as the flammability evaluation index $A_m$. The flammability evaluation index $A_m$ is expressed by the following formula (1), where $C_i$ represents the flammability class of the mixture component i and $y_i$ represents the mixture ratio of the mixture component i.

$$A_m = \sum_{i=1}^{n} C_i y_i \tag{1}$$

The flammability evaluation method according to the comparative example is realized by the mixed refrigerant flammability evaluation apparatus 10 in which the number n of mixture components and the flammability class of the mixture component i are stored in the storage unit 100 as the input parameters 110.

Figure 2:
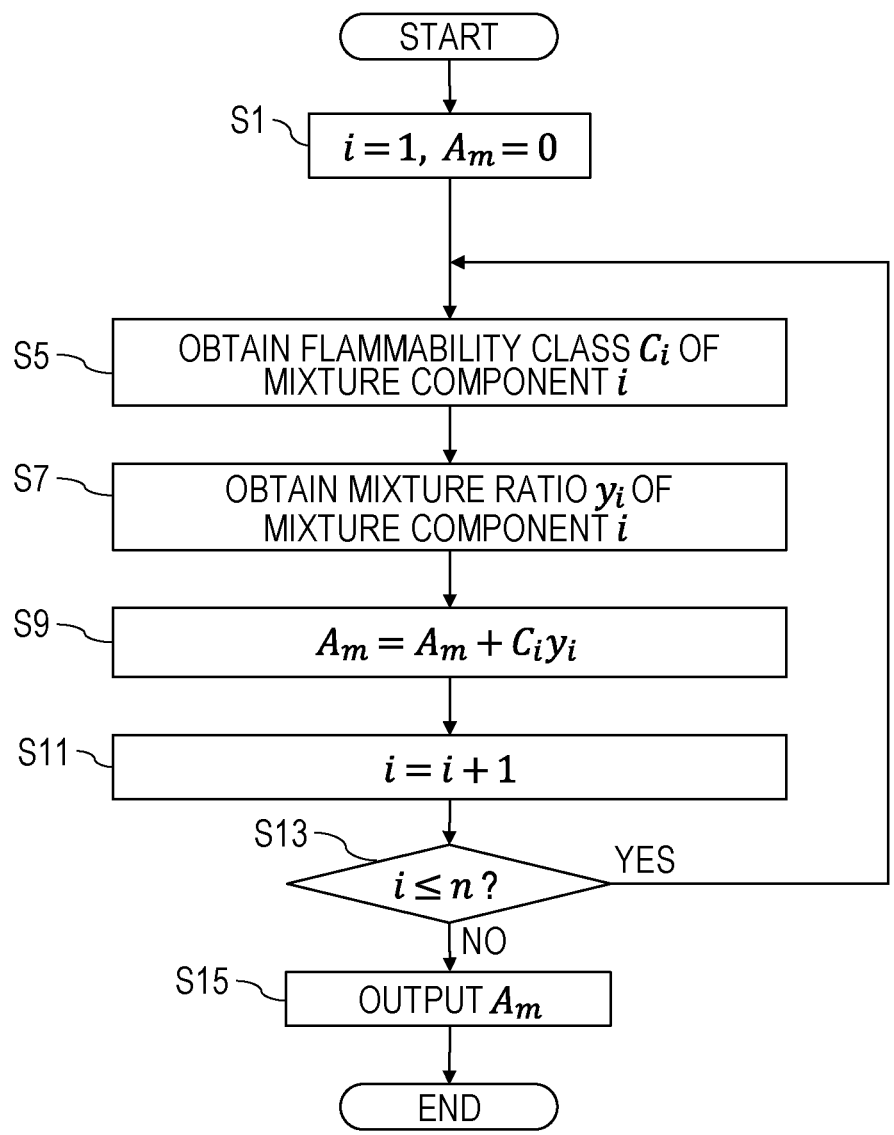
FIG. 2 is a flowchart illustrating a processing procedure according to a comparative example.

FIG. 2 is a flowchart illustrating a processing procedure according to the comparative example. As illustrated in FIG. 2, the input parameter obtaining unit 11 substitutes 1 for i and substitutes 0 for $A_m$ (step S1). i represents a mixture component contained in the mixed refrigerant material to be evaluated. $A_m$ represents the value of the evaluation target index for the mixed refrigerant material to be evaluated. Next, the input parameter obtaining unit 11 obtains the flammability class $C_i$ of the mixture component i (step S5). Next, the input parameter obtaining unit 11 obtains the mixture ratio $y_i$ of the mixture component i (step S7). Next, the flammability evaluation index calculation unit 12 performs calculation of the following formula (2) by using the flammability class $C_i$ and the mixture ratio $y_i$ obtained in steps S5 and S7 (step S9).

$$A_m = A_m + C_i y_i \tag{2}$$

$A_m$ on the right side of the formula (2) is the value of the flammability evaluation index calculated by iterative processing. Next, i is incremented (step S11). Next, it is determined whether or not i≤n holds, as a branching condition of the iterative processing (step S13). n represents the number of mixture components contained in the mixed refrigerant material to be evaluated. When i≤n holds (step S13: YES), the processing of steps S5 to S11 is repeated. When i≤n does not hold (step S13: NO), the iterative processing is ended, and the flammability evaluation index $A_m$ is output (step S15). The output flammability evaluation index $A_m$ is stored in the storage unit 100 as the output parameter 120.

Figure 3:
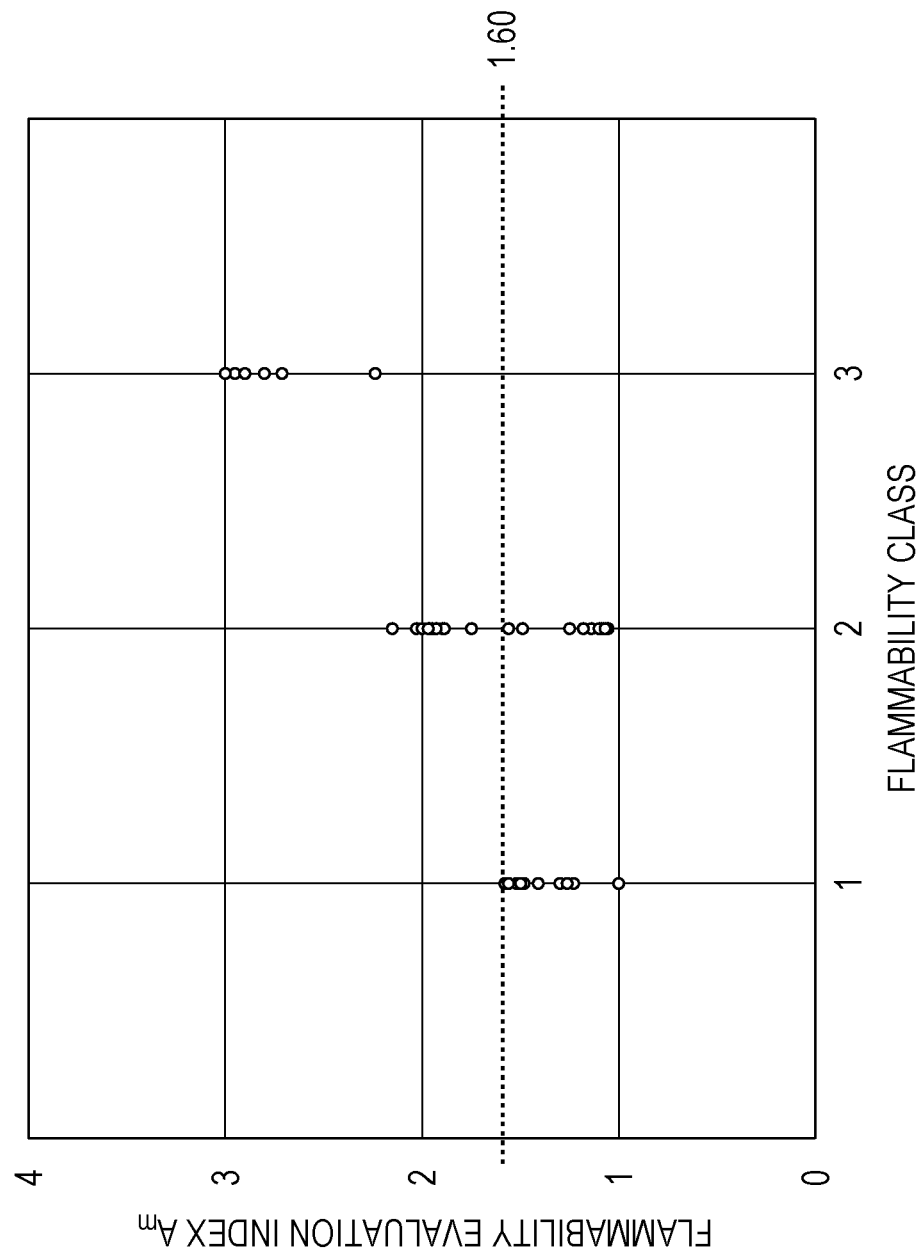
FIG. 3 is a diagram illustrating results of processing according to the comparative example.

FIG. 3 is a diagram illustrating results of processing according to the comparative example. Illustrated are results of applying the flammability evaluation method according to the comparative example to 49 existing mixed refrigerant materials whose flammability is known. The vertical axis represents the value of the flammability evaluation index $A_m$ calculated according to the processing procedure of the comparative example for the 49 existing mixed refrigerant materials. The horizontal axis represents the flammability class into which the 49 existing mixed refrigerant material are classified based on the results of the combustion experiment. The 49 existing mixed refrigerant materials are listed in Table 1 illustrated in FIGS. 9A and 9B.

In the combustion experiment, the combustion heat and the combustion limit air volume ratio are measured by igniting a flask filled with the target material. The flammability of the refrigerant material is classified based on the measured combustion heat and combustion limit air volume ratio with reference to the standards of the international standard ISO817.

As illustrated in FIG. 3, the value of the flammability evaluation index $A_m$ calculated according to the processing procedure of the comparative example is non-linear with respect to the flammability class determined by the experiment. It may be seen that although the flammability class 2 and the flammability class 3 may be distinguished from each other by setting a threshold value for the value of the flammability evaluation index $A_m$, the flammability class 1 and the flammability class 2 may not be distinguished from each other. For example, when the boundary value between the flammability class 1 and the flammability class 2 is set to $A_m=1.60$, a case where a mixed refrigerant material classified into the flammability class 2 in the experiment has a calculated flammability evaluation index $A_m$ of a value smaller than 1.60 and is predicted as the flammability class 1 occurs 11 times.

The reason why the classification error occurs 11 times is considered to be because there is a difference in flammability between pure refrigerant materials classified into the same flammability class 2.

If the classification error occurs 10 or more times when it is desired to obtain which mixed refrigerant material belongs to the flammability class 1 by prediction, time required for additional combustion experiments for verifying the prediction becomes enormous. The aforementioned combustion experiment require about 10 minutes for one mixed refrigerant material. Therefore, extra time is required for the additional combustion experiments for verifying the prediction. The flammability evaluation using the flammability evaluation index $A_m$ calculated according to the processing procedure of the comparative example of the information processing apparatus has low accuracy and is insufficient as a basis for predicting the flammability.

Next, a method for evaluating the flammability of the information processing apparatus according to the first embodiment will be described. In the flammability evaluation method according to the first embodiment, the total sum of values of respective components of the mixed refrigerant material each of which is obtained by multiplying a value obtained based on the numbers of hydrogen atoms, halogen atoms, and double bonds included in the molecular structure of the mixture component i by the mixture ratio $y_i$ of the mixture component i is calculated as the flammability evaluation index $A_m$. The flammability evaluation index $A_m$ is represented by the following formula (3), where $H_i$ represents the number of hydrogen atoms included in the molecular structure of the mixture component i, $F_i$ represents the number of halogen atoms included in the molecular structure of the mixture component i, and $d_i$ represents the number of double bonds included in the molecular structure of the mixture component i.

$$A_m = \sum_{i=1} \frac{H_i}{H_i + \alpha F_i - d_i} y_i \tag{3}$$

The larger the value of the formula (3) is, the higher the flammability of the mixed refrigerant material is. The flammability evaluation index $A_m$ is not limited to the value represented by the formula (3) described above, and may be the total sum of values each of which is obtained by multiplying a value obtained based on the numbers of hydrogen atoms, halogen atoms, and double bonds included in the molecular structure of each of the plurality of components of the mixed refrigerant material by the mixture ratio of each of the plurality of components.

In particular, based on the finding that a material including more double bonds is more flammable, it is desirable that the obtained value is inversely proportional to a value obtained by subtracting the number of double bonds from the number of single bonds included in the molecular structure, from the viewpoint of improving the accuracy of evaluation of the flammability of the mixed refrigerant material. In the formula (3), since $d_i$ is present in the denominator, the obtained value is inversely proportional to the number of single bonds included in the molecular structure, that is, to a value obtained by subtracting the number of double bonds from the number of hydrogen atoms and the number of halogen atoms. This indicates that decrease in the flammability according to increase in the number of single bonds is relieved according to the number of double bonds. When the number of single bonds increases and the molecular weight increases, the intermolecular force becomes stronger and the reactivity becomes lower. When a double bond is included in the molecular structure, since the reactivity between a double bond and oxygen is high, the flammability is higher than in the case where only single bonds are included.

Based on the finding that decrease in the flammability according to increase in the number of halogen atoms is greater than that according to increase in the number of hydrogen atoms, it is desirable that the obtained value is inversely proportional to a value obtained by subtracting the number of double bonds from the sum of the number of hydrogen atoms and a value obtained by multiplying the number of halogen atoms by a coefficient larger than 1, from the viewpoint of improving the accuracy of evaluation of the flammability of the mixed refrigerant material. In the formula (3), the number $F_i$ of halogen atoms in the denominator is multiplied by a coefficient $\alpha$ larger than 1, so that the influence of the decrease in the flammability caused by halogen may be reflected. Halogen is stronger in electronegativity than hydrogen and it is more difficult to break a bond thereof, so that the energy required for combustion is large. The influence of the number of halogen atoms on the flammability is greater than that of hydrogen, and is evaluated in the flammability evaluation index $A_m$ with a larger weight. The coefficient $\alpha$ of the formula (3) is preferably 10 or more for improving prediction accuracy.

The number $d_i$ of double bonds included in the formula (3) is represented by the following formula (4), where $C_i$ represents the number of carbon atoms contained in the molecular structure of the mixture component i.

$$d_i = \frac{(2C_i + 2 - F_i - H_i)}{2} \tag{4}$$

Figure 4:
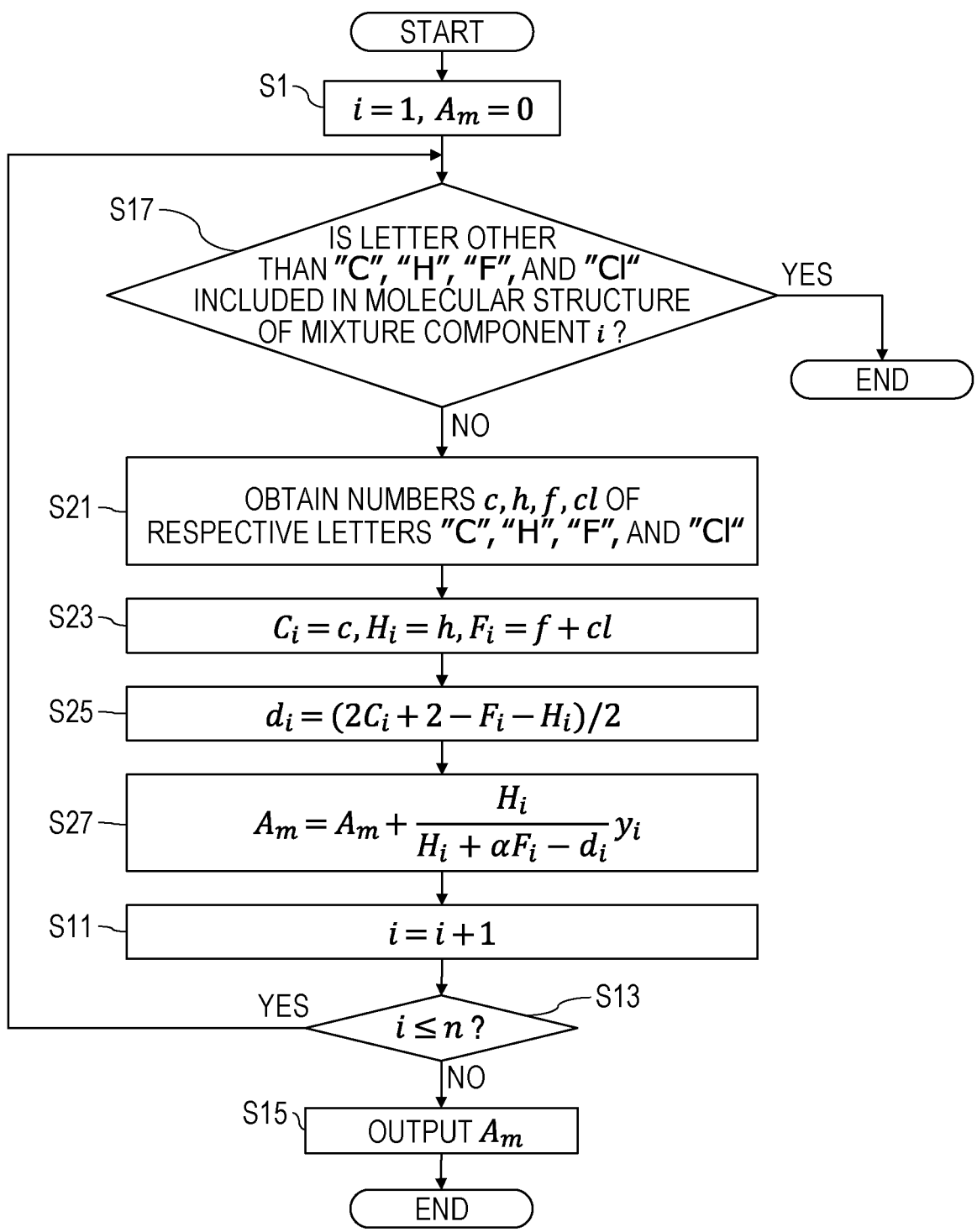
FIG. 4 is a flowchart illustrating a processing procedure performed by the information processing apparatus according to the first embodiment.

FIG. 4 is a flowchart illustrating a processing procedure performed by the information processing apparatus according to the first embodiment. The flammability evaluation method according to the first embodiment and the flammability evaluation method of the comparative example described with reference to FIG. 2 are the same in that the same reference numerals are used, but are different in the following points. In the iterative processing of steps S5 to S11 of the flowchart illustrated in FIG. 2, the input parameters 110 to be obtained and the formula indicating the flammability evaluation index $A_m$ to be calculated are different.

As illustrated in FIG. 4, the input parameter obtaining unit 11 determines whether or not a character other than "C", "H", "F", and "Cl" is included in the molecular structure of the mixture component i (step S17).

The molecular structure is determined by, for example, performing character recognition on the molecular formula of the mixture component i stored in the storage unit 100 as the input parameters 110. When the molecular structure of the mixture component i includes a character other than "C", "H", "F", and "Cl" (step S17: YES), the processing is ended. For the mixture component i containing a character other than "C", "H", "F", and "Cl" in the molecular structure, exception processing of the flammability evaluation is performed. When the molecular structure of the mixture component i does not include a character other than "C", "H", "F", "Cl" (step S17: NO), the input parameter obtaining unit 11 obtains the atom numbers c, h, f, and cl of "C", "H", "F", and "Cl", respectively (step S21). The atom numbers c, h, f, and cl may be obtained, for example, from the subscripts of the molecular formula.

The input parameter obtaining unit 11 determines the number $C_i$ of carbon atoms, the number $H_i$ of hydrogen atoms, and the number $F_i$ of halogen atoms included in the molecular structure of the mixture component i based on the atom numbers c, h, f, and cl obtained in step S21 (step S23).

The atom numbers c and h obtained in step S21 respectively correspond to the number $C_i$ of carbon atoms and the number $H_i$ of hydrogen atoms included in the molecular structure of the mixture component i, and the sum of the atom numbers f and cl corresponds to the atom number $F_i$ of halogen atoms included in the molecular structure of the mixture component i.

The flammability evaluation index calculation unit 12 calculates the number $d_i$ of double bonds included in the molecular structure of the mixture component i, by using the number $C_i$ of carbon atoms, the number $H_i$ of hydrogen atoms, and the number $F_i$ of halogen atoms included in the molecular structure of the mixture component i that are determined in step S23 (step S25).

The flammability evaluation index calculation unit 12 executes calculation of the following formula (5) by using $C_i$, $F_i$, and $d_i$ determined in steps S23 and S25 (step S27).

$$A_m = A_m + H_i/H_i + \alpha F_i - d_i y_i \quad (5)$$

$A_m$ on the right side of the formula (5) is the value of the flammability evaluation index calculated by iterative processing.

Figure 5:
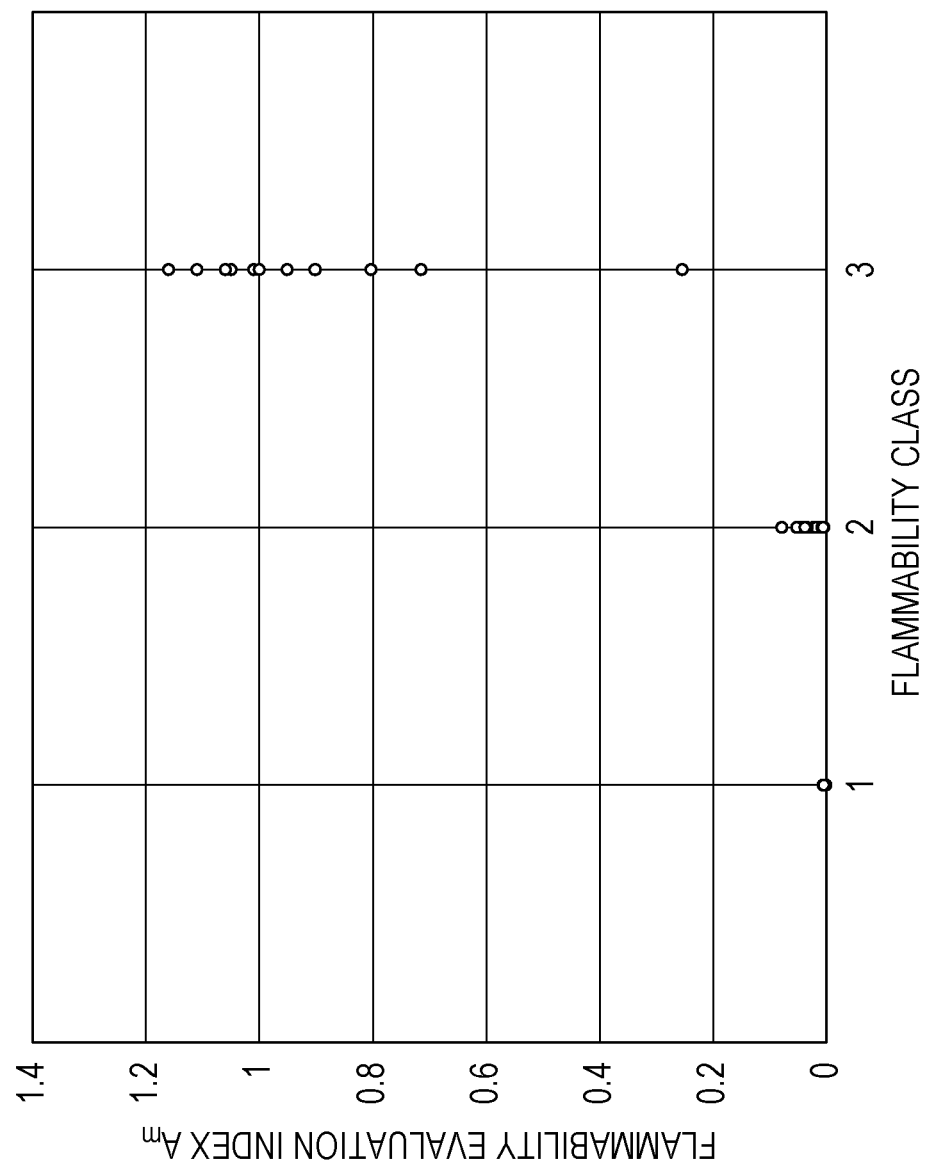
FIG. 5 is a diagram illustrating results of the processing performed by the information processing apparatus according to the first embodiment.
Figure 6:
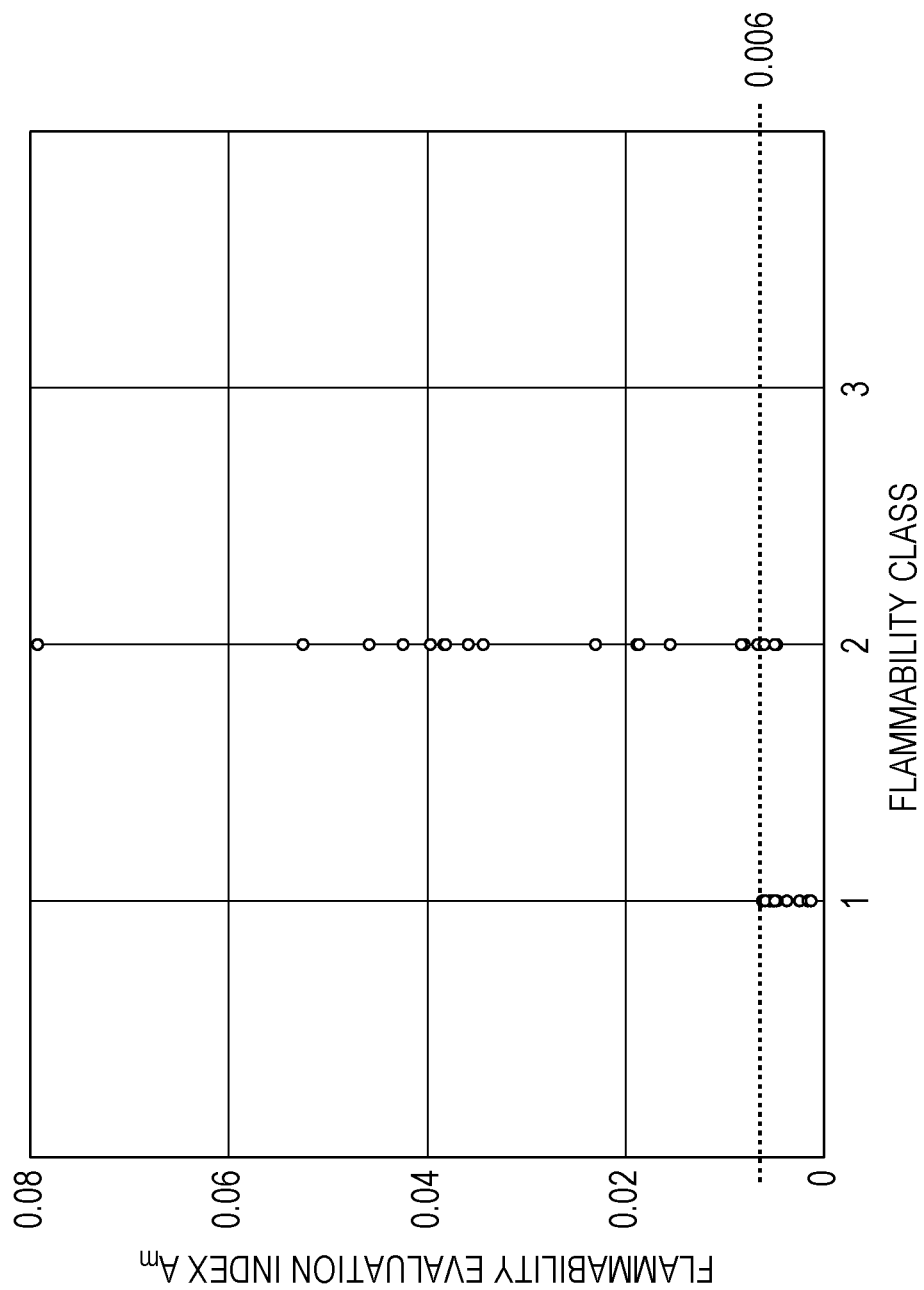
FIG. 6 is a diagram illustrating details of FIG. 5.

FIG. 5 is a diagram illustrating results of the processing performed by the information processing apparatus according to the first embodiment. FIG. 6 is a diagram illustrating details of FIG. 5. Illustrated are results of applying the flammability evaluation method performed by the information processing apparatus according to the first embodiment to 49 existing mixed refrigerant materials whose flammability is known. The vertical axis represents the value of the flammability evaluation index $A_m$ calculated according to the processing procedure performed by the information processing apparatus according to the first embodiment for the 49 existing mixed refrigerant materials. The horizontal axis represents the flammability class into which the 49 existing mixed refrigerant material are classified based on the results of the combustion experiment. The 49 existing mixed refrigerant materials are listed in Table 1 mentioned above. The coefficient α in the formula (3) is set to 100.

For example, when the boundary value between the flammability class 1 and the flammability class 2 is set to $A_m = 0.006$, a case where a mixed refrigerant material classified into the flammability class 2 in the experiment has a calculated flammability evaluation index $A_m$ of a value smaller than 0.006 and is predicted as the flammability class 1 occurs 3 times.

Since the number of classification errors is reduced, the time required for additional flammability experiments for verifying the prediction is reduced. The flammability evaluation using the flammability evaluation index $A_m$ calculated according to the processing procedure performed by the information processing apparatus of the first embodiment has higher accuracy than the comparative example.

Figure 7:
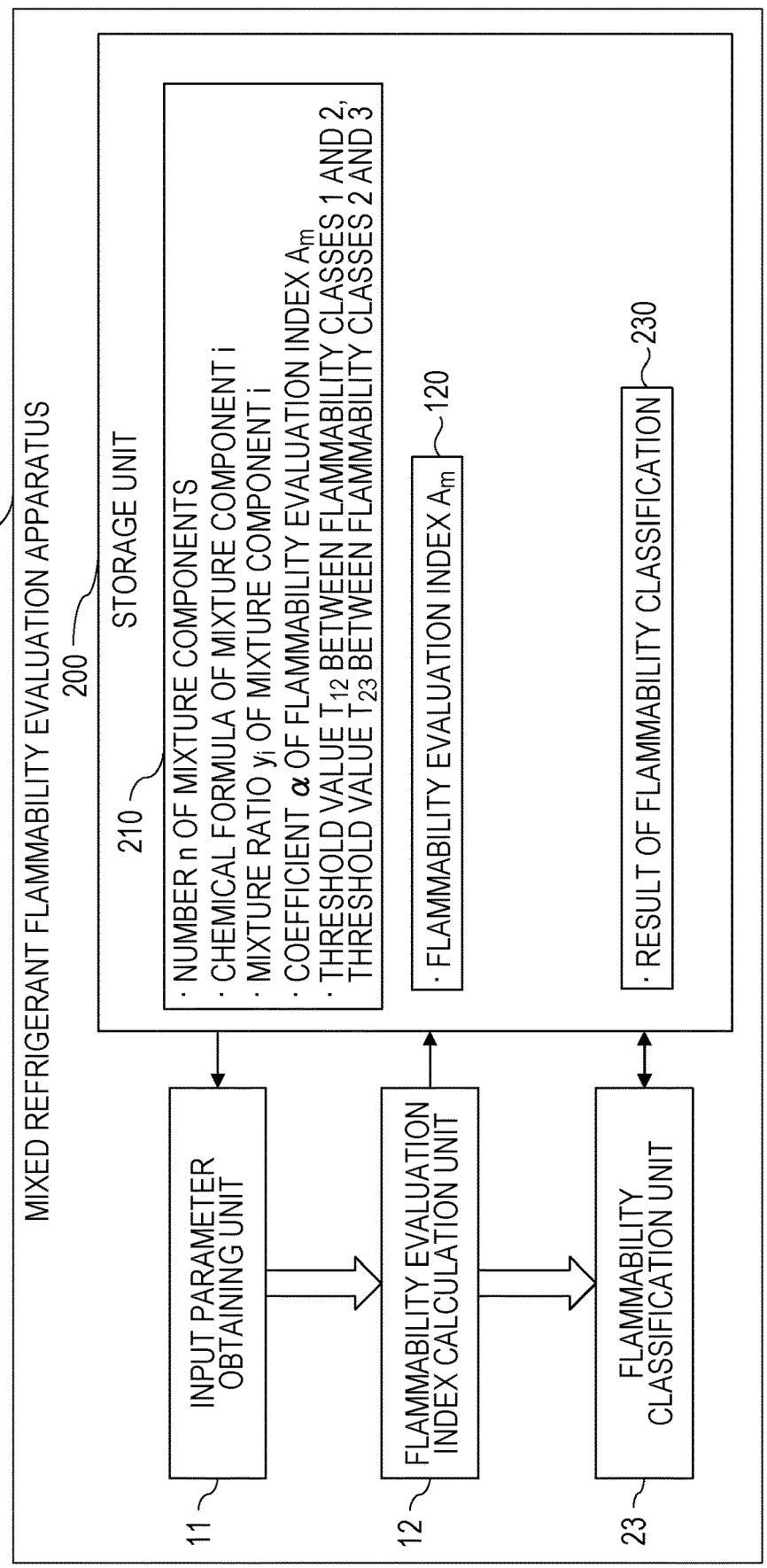
FIG. 7 is a diagram illustrating an information processing apparatus according to a second embodiment.

An information processing apparatus according to a second embodiment will be described. The information processing apparatus according to the second embodiment is an apparatus for determining the flammability class of an unknown mixed refrigerant material by calculating the flammability evaluation index $A_m$. FIG. 7 is a diagram illustrating the information processing apparatus according to the second embodiment. The information processing apparatus according to the second embodiment and the information processing apparatus described with reference to FIG. 1 are the same in that the same reference numerals are used, but are different in the following points. As illustrated in FIG. 7, a mixed refrigerant flammability classification apparatus 20 includes a storage unit 200 that stores different parameters from those in the storage unit 100 described with reference to FIG. 1. In addition to the information processing apparatus described with reference to FIG. 1, there is further provided a flammability classification unit 23 which is coupled to the flammability evaluation index calculation unit 12 and which is capable of inputting and outputting data to and from the storage unit 200.

The storage unit 200 further stores, as input parameters 210, a threshold value $T_{12}$ for distinguishing the flammability class 1 and the flammability class 2 from each other and a threshold value $T_{23}$ for distinguishing the flammability class 2 and the flammability class 3 from each other with reference to the value of the flammability evaluation index $A_m$, in addition to the input parameters 110 described with reference to FIG. 1. The storage unit 200 stores a flammability classification result of the classification by the flammability classification unit 23 as an output parameter 230. The classification by the flammability classification unit 23 will be described later.

The flammability classification unit 23 is, for example, a central processing unit (CPU).

Figure 8:
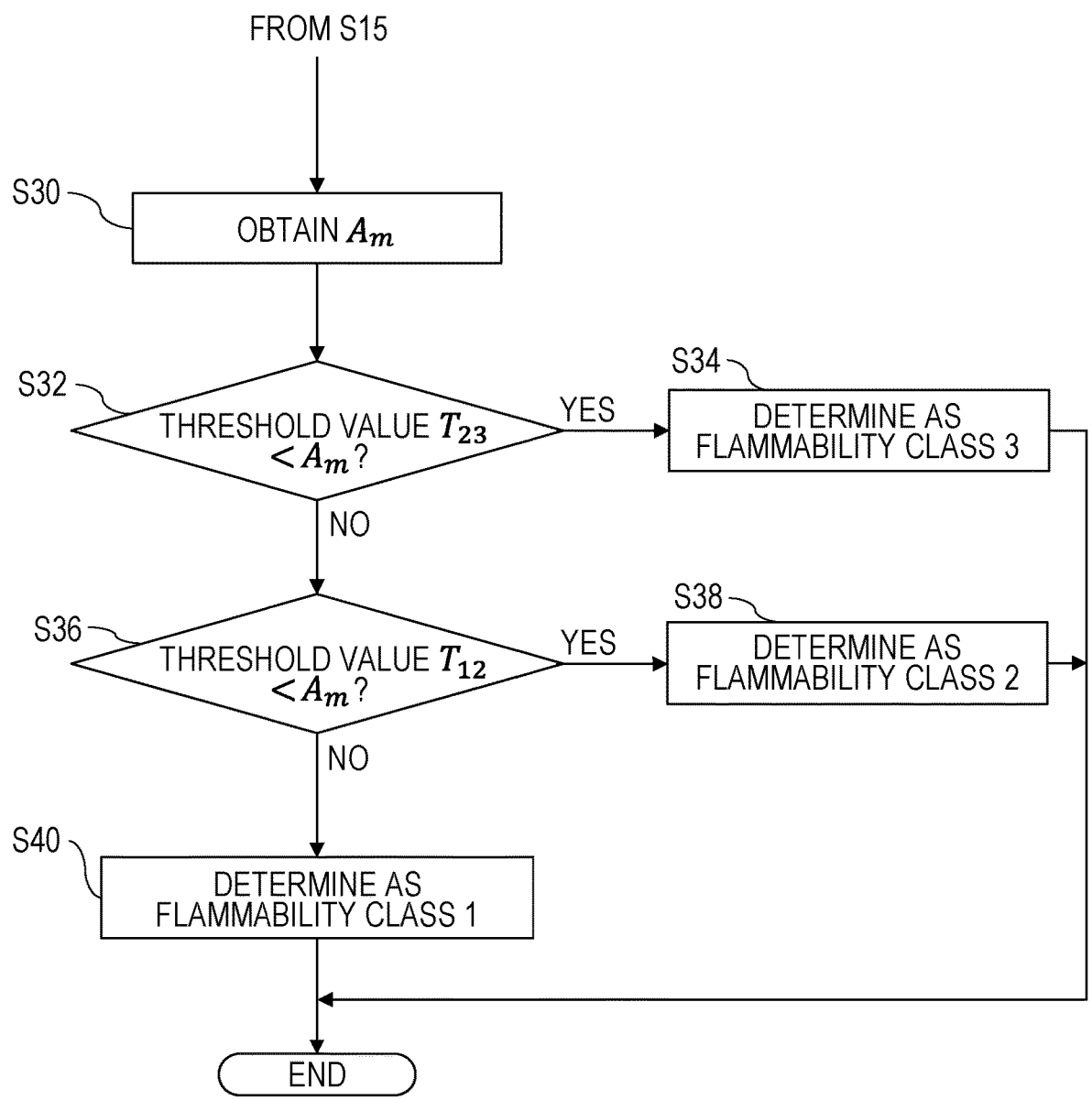
FIG. 8 is a flowchart illustrating a processing procedure performed by the information processing apparatus according to the second embodiment.

A flammability classification method performed by the information processing apparatus according to the second embodiment will be described. FIG. 8 is a flowchart illustrating a processing procedure performed by the information processing apparatus according to the second embodiment. The processing procedure illustrated in FIG. 8 is executed after the flammability evaluation method from the start up to step S15 of the processing procedure of the first embodiment described with reference to FIG. 4 is executed. The processing is started when the flammability evaluation index $A_m$ output in step S15 is stored in the storage unit 200 as the output parameter 120, and first, the flammability classification unit 23 obtains the flammability evaluation index $A_m$ from the storage unit 200 (step S30). Next, the flammability classification unit 23 determines whether or not $T_{23} < A_m$ holds for the flammability evaluation index $A_m$ obtained in step S30 and the threshold value $T_{23}$ obtained from the storage unit 200 (step S32). When $T_{23} < A_m$ holds (step S32: YES), the mixed refrigerant material is determined as belonging to the flammability class 3, this information is stored in the storage unit 200 as the flammability classification result, and the processing is ended (step S34). When $T_{23} < A_m$ does not hold (step S32: NO), the flammability classification unit 23 determines whether or not $T_{12} < A_m$ holds for the flammability evaluation index $A_m$ obtained in step S30 and the threshold value $T_{12}$ obtained from the storage unit 200 (step S36). When $T_{12} < A_m$ holds (step S36:

YES), the mixed refrigerant material is determined as belonging to the flammability class 2, this information is stored in the storage unit 200 as the flammability classification result, and the processing is ended (step S38). When $T_{12} < A_m$ does not hold (step S36: NO), the mixed refrigerant material is determined as belonging to the flammability class 1, this information is stored in the storage unit 200 as the flammability classification result, and the processing is ended (step S40). The flammability classification result is information in which the mixed refrigerant material and the determined flammability class are associated with each other, and is stored in the storage unit 200 as the output parameter 230.

The mixed refrigerant flammability classification apparatus 20 obtains the flammability evaluation index $A_m$ for an unknown mixed refrigerant material, and is capable of determining the flammability class with high accuracy.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. An information processing apparatus for evaluating flammability of a mixed refrigerant material containing a plurality of components, the information processing apparatus comprising:
    a memory; and
    a processor coupled to the memory and configured to perform to:
    calculate, for each of the plurality of components, a second value obtained by multiplying a mixture ratio thereof in the mixed refrigerant material by a first value obtained based on numbers of hydrogen atoms, halogen atoms, and double bonds included in a molecular structure thereof;
    calculate a total sum of the second value calculated for each of the plurality of components; and
    classify the mixed refrigerant material into a predetermined flammability class based on the total sum.

2. The information processing apparatus according to claim 1, wherein the first value is inversely proportional to a value obtained by subtracting the number of double bonds from a number of single bonds included in the molecular structure.

3. The information processing apparatus according to claim 1, wherein the first value is inversely proportional to a value obtained by subtracting the number of double bonds from a sum of the number of hydrogen atoms and a value obtained by multiplying the number of halogen atoms by a coefficient larger than 1.

4. The information processing apparatus according to claim 3, wherein the total sum is defined by $$A_m = \sum_{i=1} \frac{H_i}{H_i + \alpha F_i - d_i} y_i$$

where $H_i$ represents the number of hydrogen atoms in the molecular structure of a component i of the mixed refrigerant material, $F_i$ represents the number of halogen atoms in the molecular structure of the component i, $d_i$ represents the number of double bonds in the molecular structure of the component i, $\alpha$ represents the coefficient, and $y_i$ represents the mixture ratio of the component i.

5. The information processing apparatus according to claim 4, wherein the coefficient $\alpha$ is 10 or more.

6. An information processing method, performed by a computer, for evaluating flammability of a mixed refrigerant material containing a plurality of components, the method comprising:
    calculating, for each of the plurality of components, a second value obtained by multiplying a mixture ratio thereof in the mixed refrigerant material by a first value obtained based on numbers of hydrogen atoms, halogen atoms, and double bonds included in a molecular structure thereof;
    calculating a total sum of the second value calculated for each of the plurality of components; and
    classifying the mixed refrigerant material into a predetermined flammability class based on the total sum.

7. A computer readable non-transitory storage medium storing a program for causing a computer to perform a process for evaluating flammability of a mixed refrigerant material containing a plurality of components, the process comprising:
    calculating, for each of the plurality of components, a second value obtained by multiplying a mixture ratio thereof in the mixed refrigerant material by a first value obtained based on numbers of hydrogen atoms, halogen atoms, and double bonds included in a molecular structure thereof;
    calculating a total sum of the second value calculated for each of the plurality of components; and
    classifying the mixed refrigerant material into a predetermined flammability class based on the total sum.

\* \* \* \* \*